United States Patent [19]

Fujimoto et al.

[11] 4,043,992

[45] * Aug. 23, 1977

[54] METHOD FOR PREPARING ACYLATED PRODUCTS

[75] Inventors: Yasuo Fujimoto; Nobuhiro Nakamizo, both of Machida, Japan

[73] Assignee: Kyowa Hakko Kogyo Co., Ltd., Tokyo, Japan

[*] Notice: The portion of the term of this patent subsequent to Feb. 18, 1992, has been disclaimed.

[21] Appl. No.: 673,149

[22] Filed: Apr. 2, 1976

Related U.S. Application Data

[62] Division of Ser. No. 498,125, Aug. 16, 1974, Pat. No. 3,963,728, which is a division of Ser. No. 49,918, June 25, 1970, Pat. No. 3,867,424.

[30] Foreign Application Priority Data

June 30, 1969 Japan .................................. 44-51061

[51] Int. Cl.$^2$ .......................................... C07C 102/06

[52] U.S. Cl. .................... 260/112.5 R; 260/326.14 T; 260/326.2; 260/471 R; 260/471 A; 260/471 C; 260/482 R; 260/482 C; 260/518 R; 260/519; 260/534 R; 260/534 C; 260/534 F; 260/534 G; 260/534 L; 260/534 M; 260/534 S

[58] Field of Search ........... 260/471 A, 471 R, 471 C, 260/482 R, 482 C, 518 R, 519, 534 R, 534 S, 112.5 R, 309, 326.14 T, 326.2

[56] References Cited

U.S. PATENT DOCUMENTS

| | | | |
|---|---|---|---|
| 3,867,424 | 2/1975 | Fujimoto et al. | 260/471 C |
| 3,963,728 | 6/1976 | Fujimoto et al. | 260/293.74 |

OTHER PUBLICATIONS

Groggins, Unit Processes in Organic Synthesis, McGraw-Hill, New York (1958) p. 410.

*Primary Examiner*—Richard L. Raymond
*Attorney, Agent, or Firm*—Fitzpatrick, Cella, Harper & Scinto

[57] ABSTRACT

Acylation of nitrogen containing compounds utilizing esters as acylation agents in the presence of salts of substituted pyridine compounds.

12 Claims, No Drawings

METHOD FOR PREPARING ACYLATED PRODUCTS

This is a division, of application Ser. No. 498,125 now U.S. Pat. No. 3,963,728 filed 8/16/74 which in turn is a division of Ser. No. 49,918, filed 6/25/70, now U.S. Pat. No. 3,867,424.

This invention relates to acylation reactions of nitrogen-containing compounds utilizing esters as acylation agents. More specifically, this invention relates to a method for preparing compounds having a

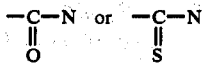

group by reacting a carboxylic acid ester, carbonic acid ester, carbamic acid ester or sulfur-analogs thereof with a nitrogen-containing compound having at least one hydrogen on said nitrogen atom in the presence of a novel catalyst. The preferred novel catalysts are metal salts or quaternary ammonium salts of a compound containing a pyridine nucleus directly substituted by a hydroxyl or mercapto group.

The use of halides or anhydrides of carboxylic acids in acylating nitrogen compounds such as amines is well known in the art. Furthermore, esters of carboxylic acids have sometimes been used as acylating agents but generally have a low reactivity and are, therefore, not practical in most cases. Recently, in peptide synthesis reactions, the so-called active esters, for example, p-nitrophenyl ester or polyhalogenated phenyl esters, have been widely utilized. The reactivities of these active esters are considerably greater than those of the ordinary alkyl esters. However, their reaction rates sometimes are low and, therefore, various catalysts for these reactions have been investigated See, for example, R. Schwyzer, M. Feurer, B. Iselin: Helv. Chim. Acta, Vol. 38, page 83 (1955), H. C. Beyerman, W. Maassen Ven den Brink: Proc. Chem. Soc., page 266 (1963), and Nakamizo: Bull. Chem. Soc. Japan, Vol. 42, pages 1,071 and 1,078 (1969). Such alkyl esters as the methyl ester, etc. are cheaper than acid halides, acid halides, acid anhydrides, active esters, etc., and it would be very advantageous if they could practically be used in acylation.

The present inventors have found that derivatives containing anions of a compound having a pyridine skeleton whose nucleus bears a hydroxyl or mercapto substituent serve as particularly effective catalysts for acylation reactions of nitrogen compounds by esters, including the so-called active esters. As counterpart cations for these anions, various metal ions and the quaternary ammonium ion are utilized. The preferred metal ions include the alkali metals, for example, lithium, sodium and potassium and the alkaline earth metals, for example, calcium. The preferred ammonium ion is a tetra substituted ion wherein the substituents are lower alkyl, for example, ethyl.

Furthermore, the pyridine nucleus can have substituent groups other than the hydroxyl and mercapto groups. Such additional substituent groups include the following; lower alkyl groups containing from 1 to 6 carbon atoms, for example, methyl, ethyl, tert-butyl and the like; aryl groups, for example, phenyl and tolyl; aralkyl groups, for example, benzyl; lower alkoxy groups containing from 1 to 6 carbon atoms, for example, methoxyl and ethoxyl; nitro groups; cyano groups and the like. It is also possible for more than one substituent to be present. Furthermore, the substituent can take the form of fused ring structures containing the pyridine nucleus together with other cyclic structures, for example, quinoline or isoquinoline.

The catalysts of the invention have been heretofore described in the literature but their use as catalysts in the process of the invention has not been described and they have an enormously high catalytic activity, as compared with previously known catalysts such as acetic acid, 2-hydroxypyridine, and 1,2,4-triazole.

In view of the diversity of industrially applicable ranges of the acylation reactions of nitrogen compounds, these For example, the following literature references teach methods for the preparation of the indicated compounds:

| Compound | Reference |
|---|---|
| 2-hydroxypyridine 4-hydroxypyridine 3-hydroxypyridine | Chemistry of Carbon Compounds, ed. by E.H. Rodd,Vol.4A, pages 544–547, Elsevier Publishing Co. |
| 6-n-amyl-2-hydroxy-pyridine | Chemical Abstracts, 47, 3309 a–d (1953) |
| 5-cyano-2-hydroxy-pyridine | Chemical Abstracts, 25, 4268 (1931) |
| 2-hydroxy-4-methoxy-pyridine | Chemical Abstracts, 50, 12044i (1956) |
| 2-hydroxy-6-phenyl-pyridine | Journal of The American Chemical Society, Vol. 59, pps. 686–689, April, 1937 |
| 2-hydroxy-6-phenethyl-pyridine | Chemical Abstracts, 36,4482 (1942) |
| 1-hydroxyisoquinoline | The Journal of Organic Chemistry Vol. 21, No. 12, pps. 1337–1341 (1957) |
| 2-mercaptopyridine | Pyridines and Its Derivatives Part IV, ed. by E. Klingsherg Interscience Publishers, pps. 349–350 (1964) |
| 4,6-dimethyl-2-hydroxypyridine | Beilstein Organische Chemie Zweites Erganzungs Werk EII 21 (H21, 49–53) |
| 2-hydroxyquinoline | Chemistry of Carbon Compounds, ed. by E.H. Rodd, Vol. 4A, pps. 620–623, Elsevier Publishing Co. |
| 2-hydroxy-5-nitro-pyridine | Beilstein Organiische Chemie Zweites Erganzungs Werk EII 21 (H21, 44–45) |

Further, the following literature references disclose various salts of pyridine and methods for their preparation:

| Salt | Reference |
|---|---|
| sodium salt of hydroxy-pyridine | Journal of the Chemical Society (1960), pps. 1232–1237 (see top of p. 1234) |
| sodium salt of hydroxy-pyridine | Chemische Berichte, Vol. 58, pps. 2650–2652 (1924) - see p. 2651 |
| sodium salt of hydroxy-pyridine | Chemistry of Carbon Compounds ed. by E.H. Rodd, Vol. 4A, Elsevier Publishing Co.,pps. 544–547 |
| potassium salt of 2-hydroxy-5-nitropyridine | Chemical Abstracts, 25, 953 (1931) |
| sodium, potassium and barium salts of hydroxy-pyridine | Pyridine and Its Derivatives, Supplement Part 3, ed. by R. A. Abramovitch, John Wiley & Sons, New York, pps. 864–867 (1974) and references cited therein. | values of high catalytic activity are very great. For example, when the preparation of the t-butyl ester of benzyloxycarbonyl-L-phenylalanylglycine from the p-nitrophenyl ester of benzyloxy-carbonyl-L-phenylalanine and t-butylester of glycine is carried out at 30° C. in anhydrous dioxane, the catalytic rate constant of acetic acid is about 50 (1.²/mol.²·min.) and that of 2-hydroxy-pyridine is about 40 (1.²/mol.²·min.), whereas the catalytic rate constant of, for example, the sodium salt of 2-hydroxy-pyridine is about 20,000 (1.²/mol.²·min.). As the catalysts of the present invention show such a high catalytic activity, the reaction time can be considerably shortened in the present invention as compared to the conventional method. Sometimes, it is even possible to effect reactions which could not be carried out by conventional methods.

The nitrogen-containing compounds useful in the present invention are amines with at least one hydrogen atom attached to the nitrogen atom, i.e., primary and secondary amines including the following: alkylamines, for example, methylamine; arylamines, for example, benzylamine and aniline; substituted arylamines, for example, nitroaniline; heterocyclic amines, for example, piperidine; hydrazines and substituted hydrazines, for example, phenylhydrazine; amides and substituted amides; and urea and substituted ureas, for example, thiourea. Other suitable nitrogen-containing compounds include hydroxylamines and substituted hydroxylamines, amino acids, peptides and the like.

The esters useful in the present invention are composed of specific acid and alcohol portions. The acid portions are preferably derived from aroyl acids, alkanoyl acids, carbonic acids, amino acids, carbamic acids and the like. The alcohol portions of the esters are derived from lower alkyl, aryl and substituted aryl alcohols and the like. Sulfur analogs of these esters are also useful in the present invention.

The method of the present invention is widely applicable to the production of various carboxylic acid amides and imides including peptides, polyamides, hydrazides, hydroxamic acids, N-acylamidines, N-acyguanidines, urea derivatives, urethane derivatives, nitrogen-containing heterocyclic compounds containing an amide bond, and the like.

Now, the present invention is explained, referring to several examples, but the applicable range of the present invention is not restricted thereto.

EXAMPLE 1

Synthesis of methyl ester of benzyloxycarbonyl-L-valyl-L-valine:

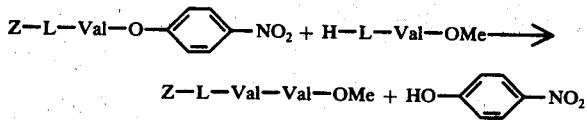

(wherein Z represents a benzyloxycarbonyl group; Val a valine residual group; Me a methyl group)

Valine methyl ester prepared from 1.7 g. of valine methyl ester hydrochloride is dissolved in 50 ml. of ethyl acetate, and 0.12 g. of the sodium salt of 2-hydroxypyridine is added thereto. Then, 3.7 g. of benzyloxycarbonyl-L-valine-p-nitrophenylester is added at room temperature, whereupon the reaction immediately starts. The reaction solution changes to yellow due to the formation of p-nitrophenol. As determined by thin layer chromatography, the reaction is almost complete in 20 minutes. Then, the reaction solution is washed once with 30 ml. of water, 5 times with 30 ml. of an aqueous 1N sodium carbonate solution, twice with 30 ml. of 1N hydrochloric acid, and finally three times with 50 ml. of water in succession, and the organic layer is dried with anhydrous sodium sulfate. After the sodium sulfate has been filtered off, the filtrate is concentrated under reduced pressure, and the residual oily matter is crystallized from ethyl acetate-petroleum benzin (1:3). Yield: 855.

| Elemental analysis: | C | H | E |
|---|---|---|---|
| Calculated ($C_{19}H_{28}N_2O_5$) | 62.62 | 7.74 | 7.69 |
| Found | 62.83 | 7.69 | 7.45 |

When the sodium salt of 6-n-amyl-2-hydroxypyridine, 5-cyano-2-hydroxypyridine, 2-hydroxy-4-methoxypyridine, 2-hydroxy-6-phenylpyridine, 2-hydroxy-6-phenethylpyridine or 1-hydroxyisoquinoline is used in place of the sodium salt of 2-hydroxypyridine, the yields of benzyloxycarbonyl-L-valyl-L-valine methyl ester are 72, 83, 81, 76, 80 and 73%, respectively.

When no catalyst is added to the reaction, it is found, by thin layer chromatography, that only a trace of the desired product is formed after 3 hours and a large amount of starting materials remain even after 92 hours.

EXAMPLE 2

Synthesis of benzyloxycarbonyl-L-phenylalanine p-nitroanilide:

2.8 g. of p-nitroaniline and 2.66 g. of the potassium salt of 2-hydroxypyridine are dissolved in 50 ml. of dimethylacetamide. Benzyloxycarbonyl-L-phenylalanine p-nitrophenyl ester in the amount of 8.4 g. is added thereto, and the solution is allowed to stand at room temperature. After 25 hours, 200 ml. of an aqueous 1N sodium carbonate solution is added thereto, and the solution is stirred for 1 hour to hydrolyze the unreacted ester. The resulting solution is extracted with 200 ml. of ethyl acetate. The organic layer is washed 6 times with 50 ml. of an aqueous 1N sodium carbonate solution, 4 times with 50 ml. of 1N hydrochloric acid, and 3 times with 70 ml. of water. After having been dried with sodium sulfate, the organic layer is concentrated. 6.1 g. of benzyloxycarbonyl-L-phenylalanine p-nitroanilide is obtained, when recrystalized form chloroform-ether. Yield: 73%, m.p. 211° C.

| Elemental analysis: | C | H | N |
|---|---|---|---|
| Calculated ($C_{23}H_{21}N_3O_5$) | 65.86 | 5.05 | 10.02 |
| Found | 66.07 | 5.43 | 10.19 |

When the potassium salt of 4-hydroxypyridine is used, the desired product is obtained in yield of 52%. No reaction takes place at all without the catalyst.

EXAMPLE 3

Sythesis of benzyloxycarbonyl-L-valine benzylamide:

1.1 ml. of benzylamine is dissolved in 200 ml. of dichloromethane, and 0.13 g. of the sodium salt of 2-mercaptopyridine is suspended therein. Then, 5.0 g. of benzyloxycarbonyl-L-valine pentachlorophenyl ester is added thereto. As determined by thin layer chromatography, the period required to consume one-half of the reactants is about 10 minutes. After 3 hours, treatment is effected in the same manner as in the previous example, and the dichloromethane layer is concentrated, whereby 3.1 g. of crude crystals are obtained (yield: 91%). By recrystallization from ethyl acetate, 2.7 g. of needle-like crystals are obtained. m.p. 174.5° C.

| Elemental analysis | C | H | N |
|---|---|---|---|
| Calculated ($C_{20}H_{24}N_2O_3$) | 70.56 | 7.11 | 8.23 |
| Found | 70.64 | 6.81 | 8.23 |

When there is no catalyst present, the time required to consume one-half of the reactants is about 1 day.

EXAMPLE 4.

Synthesis of N-benzylacetamide:

2.1 g. of benzylamine, 7.4 g. of methyl acetate and 1.5 g. of the sodium salt of 4,6-dimethyl-2-hydroxypyridine are dissolved in 30 ml. of dimethyl acetamide and heated at about 78° C. for 4.5 hours. As determined by thin layer chromatography, all but a trace of the benzylamine is consumed. 200 ml. of water and 0.9 ml. of concentrated hydrochloric acid are added to the reaction solution, and the solution is extracted three times with 100 ml. of ethyl acetate. The organic layer is washed with 100 ml. of water, and, after drying with sodium sulfate, concentrated and crystallized. After recrystallization from 300 ml. of ether-petroleum benzin (1:1), 2.5 of needle-like crystals of N-benzyl acetamide are obtained (yield: 84%).m.p. 60.5° - 62° C.

When no catalyst is employed, large amounts of unreacted benzylamine are recovered and only a very small amount of the desired product is formed.

EXAMPLE 5

Synthesis of N-(benzyloxycarbonylglycyl)-piperidine:

8.5 g. of piperidine and 1.2 g. of the sodium salt of 3-hydroxypyridine are added to 100 ml. of ethyl acetate, and 28.5 g. of benzyloxycarbonylglycine phenyl ester is added thereto with stirring at room temperature, whereupon reaction immediately starts and is complete in 2 hours. The product is worked up as previously described to give an oil which is crystallized from acetone-water. 18.7 g. of N-(benzyloxycarbonylglycyl)-piperidine are obtained (yield: 68%). m.p. 111°-112° C. A single spot is obtained therefrom by thin layer chromatography. An additional 5.9 g. of crystals are obtained from the mother liquor, (yield: 21%). m.p. 109.5°-112° C.

| Elemental analysis (first crop): | C | H | N |
|---|---|---|---|
| Calculated ($C_{15}H_{20}N_2O_3$) | 65.19 | 7.30 | 10.14 |
| Found | 65.12 | 7.50 | 10.06 |

When benzyloxycarbonylglycine thiophenyl ester is used in place of the benzyloxycarbonylglycine phenyl ester, the reaction is complete in 1 hour, and the yield of the desired product is 93%.

In the case of the phenyl ester, the crystals are obtained in a yield of only 44% when the reaction is carried out for 6.5 hours without the catalyst. It is determined by thin layer chromatography that the product is contaminated with a large amount of unreacted benzyloxycarbonylglycine phenyl ester. Thus, it is apparent that the catalyst is highly effective.

EXAMPLE 6

Synthesis of 4-amino-6-hydroxy-2-mercaptopyrimidine:

0.57 g. of ethyl cyanoacetate and 0.38 g. of thiourea are heated under reflux in 3 ml. of methanol in the presence of 1.17 g. of the sodium salt of 2-hydroxypyridine. After completion of reaction, 4 ml. of water is added, and the solution is neutralized with 0.58 ml. of acetic acid, to deposit the desired monohydrate crystals. Yield: 82%. The ultraviolet absorption spectrum agrees closely with the literature values.

When urea, guanidine or acetamidine is used in place of the thiourea, the correspondingly substituted pyrimidine is produced.

None of the desired product is produced in this reaction when the sodium salt of 2-hydroxypyridine is omitted or is replaced by an equimolar amount of triethylamine.

EXAMPLE 7

Synthesis of N-benzoyl-N'-phenylhydrazine:

2.16 g. of phenylhydrazine and 3.22 g. of benzoic acid cyanomethyl ester are heated at 50° C. for 1 hour in 10 ml. of ethanol in the presence of 1.14 g. of the calcium salt of 2-hydroxypyridine, whereby N-benzoyl-N'-phenylhydrazine is obtained in a yield of 88%, m.p. 170° C.

When the reaction is carried out without the catalyst under the same conditions, the yield is only 23%.

EXAMPLE 8

Synthesis of palmitohydroxamic acid:

14.2 g. of ethyl palmitate and 2 g. of hydroxylamine are reacted at room temperature in 300 ml. of ethanol in the presence of 1.7 g. of the sodium salt of 2-hydroxyquinoline. The reaction is complete in 5 hours, and 11.7 g, of palmitohydroxamic acid are obtained (yield: 85%), m.p. 100° - 101° C. after recrystallization from ethanol-petroleum ether(1:1).

If the catalyst is omitted, a reaction time of about two days is required.

EXAMPLE 9

Synthesis of t-butyloxycarbonyl-L-proline:

11.5 g. of L-proline is dissolved in 4N sodium hydroxide, and 100 ml. of dimethyl formamide, 50 ml. of chloroform, 10.1 g. of the lithium salt of 2-hydroxypyridine and 36.6 g. of t-butylpentachlorophenyl carbonate are added thereto. The solution is stirred at room temperature for 3 hours, after which 100 ml. of chloroform and 200 ml. of water are added. After shaking, the water layer is acidified to a pH of 2 with 1N hydrochloric acid, and extracted with 200 ml. of ethyl acetate. The product is worked up as previously described to give t-butyloxycarbonyl-L-proline in 79% yield, m.p. 137° C.

When triethylamine is used in place of the lithium salt of 2-hydroxypyridine, it requires about 20 hours to obtain the same amount of product.

EXAMPLE 10

Synthesis of N-methyl-N'-phenyl urea:

15.1 g. of phenyl N-methylcarbamate, 9.3 g. of aniline and 5.4 g. of the tetraethylammonium salt of 2-hydroxy-5-nitro-pyridine are refluxed in 200 ml. of ethanol for 5 hours. The reaction solution is concentrated, and the residue is dissolved in 100 ml. of chloroform, washed successively with 50 ml. of 1N sodium carbonate, 50 ml. of 1N hydrochloric acid and 100 ml. of water, and dried. By concentrating to dryness and recrystallizing from 120 ml. of ethanol, crystals of N-methyl-N- phenylurea having a m.p. of 150° – 151° C. are obtained in 91% yield.

When phenyl N-methyldithiocarbamate is used in place of phenyl N-methylcarbamate, N-methyl-N'-phenylthiourea is obtained in 79% yield, m.p. 113° C. In either case, the reaction rate is considerably lower without the catalyst than with the catalyst.

What is claimed is:

1. In a process for preparing a carboxylic acid amide which comprises acylating an amino acid or ester thereof with an ester derived from an aliphatic or aromatic carboxylic acid, the improvement which comprises carrying out said acylation in the presence of an alkali-metal salt, an alkaline earth metal salt or a quaternary ammonium salt of a pyridine compound whose pyridine nucleus is directly substituted by a hydroxy group or a mercapto group, and optionally by at least one member selected from the group consisting of an alkyl group having from 1 to 6 carbon atoms, an aryl group, an aralkyl group, an alkoxy group having from 1 to 6 carbon atoms, a nitro group, a cyano group and an unsubstituted benzene ring which is fused to the pyridine nucleus.

2. The process of claim 1 wherein the pyridine compound is pyridine, quinoline or isoquinoline.

3. The process of claim 1 wherein the acylation is carried out in the presence of a salt of a hydroxypyridine.

4. The process of claim 1 wherein said ester of amino acid is valine methyl ester.

5. The process of claim 1 wherein said ester of amino acid is valine methyl ester, and wherein said ester derived from a carboxylic acid is benzyloxycarbonyl-L-valine-p-nitrophenyl ester.

6. The process of claim 1 wherein said aryl group is phenyl or tolyl.

7. The process of claim 1 wherein said aralkyl group is benzyl.

8. The process of claim 1 wherein said quaternary ammonium salt is a lower alkyl tetra-substituted quaternary ammonium salt.

9. The process of claim 3 wherein said salt is a sodium salt.

10. The process of claim 9 wherein said sodium salt is selected from the group consisting of sodium salts of 2-hydroxypyridine, 6-n-amyl-2-hydroxypyridine, 5-cyano-2-hydroxypyridine, 2-hydroxy-4-methoxypyridine, 2-hydroxy-6-phenylpyridine, 2-hydroxy-6-phenethylpyridine and 1-hydroxyisoquinoline.

11. The process of claim 1 wherein said pyridine nucleus of said pyridine compound is directly substituted by only a hydroxy group or a mercapto group.

12. The process of claim 1 wherein said pyridine nucleus of said pyridine compound is directly substituted by a hydroxy group or a mercapto group, and also by at least one member selected from the group consisting of an alkyl group having from 1 to 6 carbon atoms, an aryl group, an aralkyl group, an alkoxy group having from 1 to 6 carbon atoms, a nitro group, a cyano group and an unsubstituted benzene ring which is fused to the pyridine nucleus.

* * * * *

UNITED STATES PATENT OFFICE
CERTIFICATE OF CORRECTION

Patent No. 4,043,992             Dated August 23, 1977

Inventor(s) YASUO FUJIMOTO, ET AL      Page 1 of 2

It is certified that error appears in the above-identified patent and that said Letters Patent are hereby corrected as shown below:

Column 1, line 36    insert a period after "investigated" and before "See"

Column 1, line 42    delete "acid halides," second occurrence

Column 2,            delete lines 11-13 in their entirety and reinsert same between the end of the table in Column 2 and line 60

Column 4, line 2     change "855" to read --85%--

Column 4, line 5     in the heading of the table, change "E" to read --N--

Column 4, line 54    change "Sythesis" to read --Synthesis--

UNITED STATES PATENT OFFICE
CERTIFICATE OF CORRECTION

Patent No. 4,043,992  Dated August 23, 1977

Inventor(s) YASUO FUJIMOTO, ET AL  Page 2 of 2

It is certified that error appears in the above-identified patent and that said Letters Patent are hereby corrected as shown below:

Column 5, line 24  insert --g.-- after "2.5" and before "of".

Signed and Sealed this

Seventeenth Day of January 1978

[SEAL]

Attest:

RUTH C. MASON  
Attesting Officer

LUTRELLE F. PARKER  
Acting Commissioner of Patents and Trademarks